US011577045B2

(12) United States Patent
Perry et al.

(10) Patent No.: US 11,577,045 B2
(45) Date of Patent: Feb. 14, 2023

(54) VIBRATORY DEVICES FOR PHANTOM LIMB PAIN

(71) Applicant: University of Pittsburgh—Of the Commonwealth System of Higher Education, Pittsburgh, PA (US)

(72) Inventors: Brianna Perry, Wareham, MA (US); Goeran Fiedler, Pittsburgh, PA (US); Kevin Charles Quinn, Tempe, AZ (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 111 days.

(21) Appl. No.: 17/014,516

(22) Filed: Sep. 8, 2020

(65) Prior Publication Data

US 2021/0069458 A1   Mar. 11, 2021

Related U.S. Application Data (60) Provisional application No. 62/897,979, filed on Sep. 9, 2019.

(51) Int. Cl.
*A61M 21/00* (2006.01)
*A61F 2/80* (2006.01)
*A61F 2/78* (2006.01)

(52) U.S. Cl.
CPC .............. *A61M 21/00* (2013.01); *A61F 2/80* (2013.01); *A61F 2002/785* (2013.01); *A61M 2021/0022* (2013.01); *A61M 2205/0216* (2013.01); *A61M 2205/8243* (2013.01); *A61M 2209/088* (2013.01)

(58) Field of Classification Search
CPC ........ A61F 2002/5058–5064; A61F 2002/785; A61F 2/7812; A61F 2/80; A61M 2021/0022

See application file for complete search history.

(56) References Cited

U.S. PATENT DOCUMENTS

| 9,949,890 | B2 | 4/2018 | Choudhury | |
| 2017/0354367 | A1* | 12/2017 | Laghi | A61B 5/6811 |
| 2018/0020973 | A1 | 1/2018 | Hurley | |
| 2018/0303704 | A1 | 10/2018 | Idris | |
| 2021/0113356 | A1* | 4/2021 | Laszczak | A61F 2/76 |
| 2021/0186718 | A1* | 6/2021 | Brandstatter | A61F 2/80 |

FOREIGN PATENT DOCUMENTS

WO    WO-2018022075 A1 *  2/2018

OTHER PUBLICATIONS

Mcginnis, Kate et al., Effect of Vibration on Pain Response to Heel Lance; Advances in Neonatal Care, vol. 16, No. 6 , pp. 439-448.
Lundeberg, T., Relief of pain from a phantom limb by peripheral stimulation, J Neurol (1985) 232 : 79-82.

\* cited by examiner

*Primary Examiner* — Thaddeus B Cox
(74) *Attorney, Agent, or Firm* — Bartony & Associates, LLC (57) ABSTRACT

A prosthetic device includes a flexible interface configured to conform to a residual limb of a user, a prosthetic socket including an outer shell more rigid than the flexible interface and positioned external to at least a portion of the flexible interface, and one or more vibrational devices placed in connection with the flexible interface to impart vibration to the residual limb.

20 Claims, 4 Drawing Sheets

VIBRATORY DEVICES FOR PHANTOM LIMB PAIN

CROSS-REFERENCE TO RELATED APPLICATIONS

This application claims benefit of U.S. Provisional Patent Application Ser. No. 62/897,979, filed Sep. 9, 2019, the disclosure of which is incorporated herein by reference.

BACKGROUND

The following information is provided to assist the reader in understanding technologies disclosed below and the environment in which such technologies may typically be used. The terms used herein are not intended to be limited to any particular narrow interpretation unless clearly stated otherwise in this document. References set forth herein may facilitate understanding of the technologies or the background thereof. The disclosure of all references cited herein are incorporated by reference.

Phantom limb pain and volume fluctuations are common issues among the population of individuals with amputations. Phantom limb pain can cause extreme discomfort to the patient and lead to other issues such as depression. Pain leads to less compliance of using their device, which promotes a sedentary lifestyle, in turn resulting in depression.

SUMMARY

In one aspect, a prosthetic device includes a flexible interface configured to conform to a residual limb of a user, a prosthetic socket including an outer shell more rigid than the flexible interface and positioned external to at least a portion of the flexible interface, and one or more vibrational devices placed in connection with the flexible interface to impart vibration to the residual limb. In a number of embodiments, the one or more vibrational devices are incorporated within the flexible interface. In a number of embodiments, the one or more vibrational devices are embedded within the flexible interface. The flexible interface is fabricated from a flexible, elastomeric polymeric material such as a silicone or a polyurethane. In a number of embodiments, the flexible interface is fabricated from silicone.

In a number of embodiment, the device further includes electronic circuitry in operative connection with the one or more vibrational devices to control operation thereof. The electronic circuitry may, for example, be configured to communicate with a personal communication device including a control algorithm stored therein to control operation of the one or more vibrational devices. The one or more vibrational devices may, for example, have a profile no greater than the thickness of the flexible interface. In a number of embodiments, the one or more vibrational devices have a profile no greater than approximately 6 mm.

The one or more vibrational devices may, for example, include one or more vibrational motors. The one or more vibrational devices may, for example, include one or more vibrational pads wirelessly coupled (for example, via inductive or magnetic coupling) to an energy source exterior to the flexible interface.

The device may further include one or more sensors in operative connection with the electronic circuitry to measure at least one of a parameter of the user, an environmental parameter, or an operational parameter of the one or more vibrational devices. The device hereof may, for example, be controlled on the basis of one or more such measured parameters (for example, via feedback or other control).

In another aspect, a method of providing vibrational therapy to a user includes placing a flexible interface configured to conform to a residual limb of the user in operative connection with the user's residual limb, the flexible interface having one or more vibrational devices in operative connection with the flexible interface to provide vibrational energy to the residual limb, providing a prosthetic socket comprising an outer shell more rigid than the flexible interface and positioned external to at least a portion of the flexible interface, and imparting vibration to the residual limb via the one or more vibrational devices.

As described above, the one or more vibrational devices may be incorporated within the flexible interface. The one or more vibrational devices may, for example, be embedded within the flexible interface. As also described above and elsewhere herein, the flexible interface is fabricated from a flexible, elastomeric polymeric material such as polyurethane or silicone.

The method may further include providing electronic circuitry in operative connection with the one or more vibrational devices to control operation thereof. The electronic circuitry may, for example, be configured to communicate with a personal communication device including a control algorithm stored therein to control operation of the one or more vibrational devices. The one or more vibrational devices have a profile no greater than the thickness of the flexible interface in a number of embodiments. The one or more vibrational devices may, for example, have a profile no greater than approximately 6 mm.

The one or more vibrational devices may, for example, include one or more vibrational motors. The one or more vibrational devices may, for example, include one or more vibrational pads wirelessly coupled to an energy source outside of the flexible interface.

In a number of embodiment, the method further includes providing one or more sensors in operative connection with the electronic circuitry to measure at least one of a parameter of the user, an environmental parameter, or an operational parameter of the one or more vibrational devices. As described herein, the device hereof may, for example, be controlled on the basis of one or more such measured parameters (for example, via feedback or other control). The electronic circuitry may, for example, be configured to communicate with a personal communication device including a control algorithm stored therein to control operation of the one or more vibrators.

In a further aspect, a flexible interface for use with a prosthetic device includes one or more vibrational devices embedded within the flexible interface to impart vibration to the residual limb. The flexible interface has a conformation to conform to a residual limb (on a first side thereof) and to an internal wall of a shell of a prosthetic socket of the prosthetic device (on a second side thereof) which is more rigid than the flexible interface and positioned external to at least a portion of the flexible interface. The flexible interface may, for example, be fabricated from a flexible, elastomeric polymeric material. The flexible interface may be further characterized as described above and elsewhere herein.

The present devices, systems, and methods, along with the attributes and attendant advantages thereof, will best be appreciated and understood in view of the following detailed description taken in conjunction with the accompanying drawings.

DETAILED DESCRIPTION

It will be readily understood that the components of the embodiments, as generally described and illustrated in the figures herein, may be arranged and designed in a wide variety of different configurations in addition to the described representative embodiments. Thus, the following more detailed description of the representative embodiments, as illustrated in the figures, is not intended to limit the scope of the embodiments, as claimed, but is merely illustrative of representative embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

As used herein and in the appended claims, the singular forms "a," "an", and "the" include plural references unless the context clearly dictates otherwise. Thus, for example, reference to "a vibrator" includes a plurality of such vibrators and equivalents thereof known to those skilled in the art, and so forth, and reference to "the vibrator" is a reference to one or more such vibrators and equivalents thereof known to those skilled in the art, and so forth. Recitation of ranges of values herein are merely intended to serve as a shorthand method of referring individually to each separate value falling within the range. Unless otherwise indicated herein, and each separate value, as well as intermediate ranges, are incorporated into the specification as if individually recited herein. All methods described herein can be performed in any suitable order unless otherwise indicated herein or otherwise clearly contraindicated by the text.

The terms "electronic circuitry", "circuitry" or "circuit," as used herein include, but is not limited to, hardware, firmware, software, or combinations of each to perform a function(s) or an action(s). For example, based on a desired feature or need. a circuit may include a software controlled microprocessor, discrete logic such as an application specific integrated circuit (ASIC), or other programmed logic device. A circuit may also be fully embodied as software. As used herein, "circuit" is considered synonymous with "logic." The term "logic", as used herein includes, but is not limited to, hardware, firmware, software, or combinations of each to perform a function(s) or an action(s), or to cause a function or action from another component. For example, based on a desired application or need, logic may include a software controlled microprocessor, discrete logic such as an application specific integrated circuit (ASIC), or other programmed logic device. Logic may also be fully embodied as software.

The term "processor," as used herein includes, but is not limited to, one or more of virtually any number of processor systems or stand-alone processors, such as microprocessors, microcontrollers, central processing units (CPUs), and digital signal processors (DSPs), in any combination. The processor may be associated with various other circuits that support operation of the processor, such as random access memory (RAM), read-only memory (ROM), programmable read-only memory (PROM), erasable programmable read only memory (EPROM), clocks, decoders, memory controllers, or interrupt controllers, etc. These support circuits may be internal or external to the processor or its associated electronic packaging. The support circuits are in operative communication with the processor. The support circuits are not necessarily shown separate from the processor in block diagrams or other drawings.

The term "controller," as used herein includes, but is not limited to, any circuit or device that coordinates and controls the operation of one or more input and/or output devices. A controller may, for example, include a device having one or more processors, microprocessors, or central processing units capable of being programmed to perform functions.

The term "logic," as used herein includes, but is not limited to, hardware, firmware, software, or combinations thereof to perform a function(s) or an action(s), or to cause a function or action from another element or component. Based on a certain application or need, logic may, for example, include a software controlled microprocess, discrete logic such as an application specific integrated circuit (ASIC), or other programmed logic device. Logic may also be fully embodied as software. As used herein, the term "logic" is considered synonymous with the term "circuit."

The term "software," as used herein includes, but is not limited to, one or more computer readable or executable instructions that cause a computer or other electronic device to perform functions, actions, or behave in a desired manner. The instructions may be embodied in various forms such as routines, algorithms, modules, or programs including separate applications or code from dynamically linked libraries. Software may also be implemented in various forms such as a stand-alone program, a function call, a servlet, an applet, instructions stored in a memory, part of an operating system or other type of executable instructions. It will be appreciated by one of ordinary skill in the art that the form of software is dependent on, for example, requirements of a desired application, the environment it runs on, or the desires of a designer/programmer or the like.

As used herein, the term "vibrator" refers to a device to generate vibration. Such devices may, for example, include piezoelectric devices, motor-driven vibratory devices, and the like. As used herein, the terms "prosthesis", "prosthetic" and the like refers to a device or methodology for replacement of a missing body part.

Vibrational energy has been explored for use in pain reduction in various settings. While vibration therapy (VT) has been used to treat acute pain in certain applications such as injections, dentistry, there is no technology that targets chronic phantom limb pain through the use of VT in connection with a prosthetic device. In a number of embodiments hereof control algorithms are used to leverage the unique capabilities of an integrated system for an effective application of VT to phantom limb pain and or volume fluctuation in connection with use of a prosthetic device.

As discussed above, in a number of embodiments, devices, systems and methods hereof apply vibration therapy to help treat volume fluctuations and/or phantom limb pain in, for example, amputees. Vibration therapy has been shown to influence muscle activity and improve vascularity. The therapy also reduces the potential for developing neuroma and aids in developing new neuronal pathways to occupy the lack thereof. To be effective, the vibration therapy component (hardware) may, for example, be integrated into a prosthesis liner, between the patient's skin and prosthesis. The devices or systems hereof can, for example, be activated in a predetermined of programmed manner by a wired or wireless control (for example, via a switch or via BLUETOOTH smartphone connectivity) throughout the day without having to remove the prosthesis. Bluetooth is a wireless technology standard for exchanging data between fixed and mobile devices over short distances using short-wavelength UHF radio waves. BLUETOOTH is managed by the Bluetooth Special Interest Group (SIG). The integration of the device or system hereof with a prosthesis liner provides significant advantages. Moreover, associated control algorithms may be readily optimized for an individual and/or group or population based on continuing patient studies.

In a number of embodiments of devices hereof, one or more vibrators are placed in connection with a flexible interface or liner which is configured to conform to a residual limb to impart vibration to the residual limb. The one or more vibrators may, for example, be positioned so that at least a portion of the flexible interface or liner is positioned between the one or more vibrators and the residual limb when the device is worn by the user/patient. In a number of embodiments, a device hereof may further include an outer shell or housing which may, for example, be designed or configured to conform the residual limb. The outer shell may, for example, be relatively rigid. The flexible interface or liner hereof may, for example, positioned within the outer shell to form a soft, flexible liner for at least a portion thereof.

The one or more vibrators may, for example, be positioned within the flexible liner. In a number of embodiments, the one or more vibrators have a low profile to reduce or minimize the thickness of the flexible liner. In general, liners for prosthetic come in different wall thicknesses. Most commonly, the liner thickness is between approximately 3 and approximately 6 mm. However, there are indications for thinner liners as well (2 mm or even 1 mm). There are also tapered or progressive profiles. The build height of the vibrational devices/motors inevitably limits how thin the liner wall can be without parts of the hardware protruding and interfering with socket fit. Vibrational motors or other vibrational mechanisms/devices hereof may be custom fabricated or commercially available. The size/build height of such vibrational devices is correlated with their performance. Because of decreased output of vibrational energy being associated with vibrational devices of smaller dimension, a plurality of or an array of small vibrational device may be needed to achieve the same effect as a single, larger vibrational device given limitations on liner thickness and corresponding limitations on the height of the vibratory devices. In a number of embodiments hereof, vibrational devices (for example, vibrational motors) have a height of no more than 6 mm or no more than 5 mm.

Figure 1:
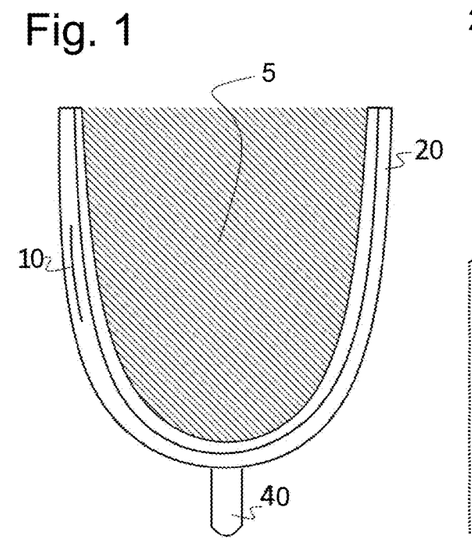
FIG. 1 illustrates a cross-sectional view of an embodiment of a device hereof incorporated or integrated in a prosthetic device socket interface or liner.
Figure 2:
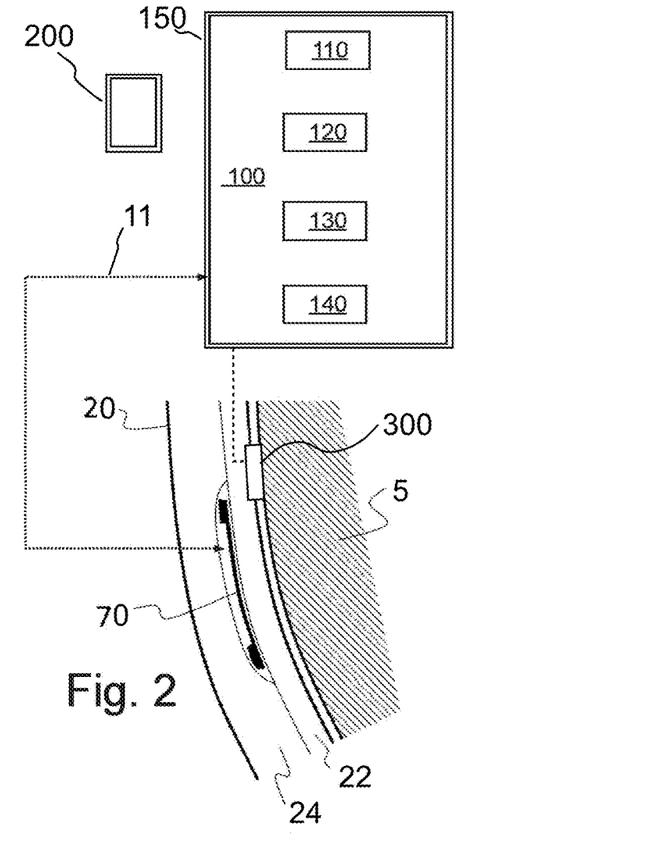
FIG. 2 illustrates an enlarged, cross-sectional view of the interface or liner of FIG. 1.
Figure 3:
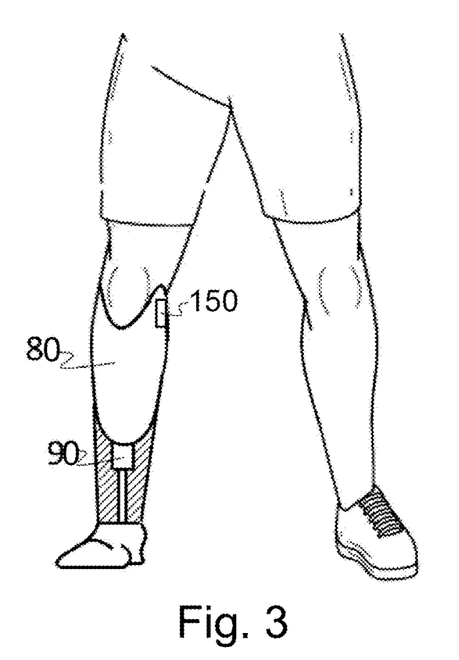
FIG. 3 illustrates the prosthetic device of FIG. 1 worn by a user.

In a number of embodiments, the devices or system hereof are advantageously integrated into a prosthetic interface or liner. As illustrated in FIGS. 1 through 3, for example, device 10 hereof may include vibrational components integrated into a conventional prosthesis liner 20 (see, FIG. 1). Such soft, flexible liners 20 are worn inside an outer shell in the form of a rigid outer socket 80 (see, FIG. 3) by many people with upper or lower limb loss. Full contact of such outer sockets 80 with the residual limb 5, along with a suspension mechanism (for example, a pin 40 and cooperating lock 90 system) provides for a reliable and comfortable connection between the limb and the prosthesis. Vibrators such as small vibration motors 70 may, for example, be installed in liner 20 without affecting the overall thickness of liner 20, and without substantially affecting flexibility and elasticity or flexibility of liner 20 (see, for example, FIG. 2).

Figure 4:
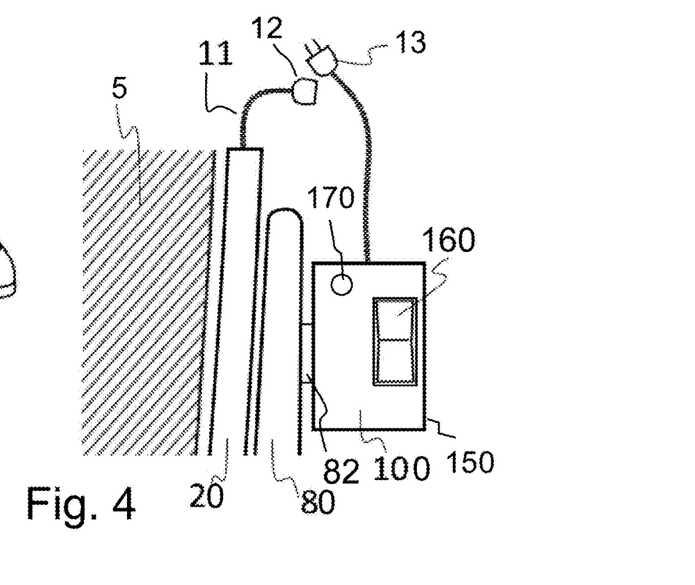
FIG. 4 illustrates an embodiment of a connection of an external control unit to one or more vibrators of a device hereof.

In one embodiment, a "sandwich" design may, for example, be used for liner 20 wherein an inner layer 22 thereof (which may, for example, be thinner) and an outer layer 24 thereof (which may, for example, be thicker) are fused together while leaving space for the placement of the vibration motor 70 or other vibrator and any attendant components or hardware. Electrical/conductive wires 11 (shown schematically in broken lines FIG. 2) for power supply to, for example, vibration motors 70 may, for example, be embedded within liner 20 in the same manner. Such electrical/conductive wires 11 may, for example, following a meandering path to accommodate stretch if needed. Electrical/conductive wires 11 may, for example, terminate in a plug or connector 12 at the liner's proximal end (see FIG. 4). Electronic circuitry 100 including a power supply 110, controller or control system (for example, including a processor or processors such as a microprocessor 120 and an associated memory system 130), and a wired or wireless (for example, BLUETOOTH) antenna or transceiver 140 may, for example, be housed in a small housing unit 150 outside of the liner 20 (see, for example, FIG. 2). Housing unit 150 may, for example, be attached to the outer side of the outer shell or rigid socket 80 (see, for example, FIG. 3). A connector plug 13 may facilitate the connection to the liner-embedded wires (see FIG. 4). Housing unit 150 may, for example, include a toggle switch 160 to manually activate the vibration motors (see FIG. 4).

The vibrational devices hereof may alternatively be magnetic or inductive vibrators that include one or more components that are at least partly installed in/or the inner wall of socket 80, adjacent to liner 20. In such embodiment, only a vibrational plate or pad (for example, represented schematically in FIG. 7 discussed below) may, for example, be embedded in liner 20 and the actuator and wiring may be placed in operative connection with the rigid prosthesis components such as socket 80.

In a number of embodiments, control the vibration function by the user may be effected through a personal communication device 200 (illustrated schematically in FIG. 2), which may, for example, provide for the setting or definition of different activation patterns and schedules. As used herein, the term "personal communications device" refers generally to mobile devices which include a communication system, a processor system, one or more user interfaces (for example, a visual feedback system including a touchscreen or other display, an auditory feedback system, and/or a tactile feedback system etc.) and an operating system capable of running general-purpose applications. Examples of personal communications devices include, but are not limited to, smartphones, tablet computers and custom devices. As used herein, the term "tablet computer" or tablet, refers to a mobile computer with a communication system, a processor system, at least one user interface as described above (typically including a touchscreen display), and an operating system (for example, an ANDROID® or iOS® operating system) capable of running general-purpose and specially developed custom applications in a single unit. As used herein, the term "smartphone" refers to a cellular telephone including a processor system, at least one user interface as described above (typically including a touchscreen display), and an operating system capable of running general-purpose and specially developed custom applications. Such personal communication devices are typically powered by rechargeable batteries and are housed as a single, mobile unit. A number of representative embodiments of systems and/or methods hereof may, for example, include a smartphone with customized user interface software to form at least a portion of the control system.

The number and position of vibrators such as vibration motors within the liner may be optimized according to the geometry of a given residual limb and the user's preference. Amplitude, frequency, and duration of vibration interventions are likewise customizable. In one example of an embodiment hereof, in a trans-tibial prosthesis, a single vibration motor (3.8 V; 12,000 RPM) is placed strategically in an area of the residual limb that is known to be receptive to the stimulus (for example, distal of the fibular head over the peroneal nerve). The default vibration frequency of the motor may, for example, be 200 Hz, providing an intensive localized stimulus without disrupting whole body balance or comfort. The external component housing in this example may, for example, be attached by a hook-and-loop type attachment mechanism (for example, VELCRO) to the knee sleeve that is part of the prosthesis and extends to the thigh. The power source may, for example, include a rechargeable cell phone battery (3.7 V; 2000 mAh) that is encompassed by the housing.

Vibrational devices may additionally or alternatively be powered mechanically (for example, spring-loaded). Energy for vibrational devices hereof and/or control thereof may be harvest from the environment (for example, solar/light energy) and/or from the human body/activity. A mechanically powered (for example, spring-loaded) device may, for example, be "wound" or energized by normal prosthesis use/user activity (for example, movement) and be activated by mechanical switch. Likewise, user activity may be converted to electrical energy as known in the energy harvesting arts.

The controller module may, for example, include an ARDUINO BLUETOOTH board (available from Arduino of Somerville, Massachusetts) programmed to output different sequences of motor activation (for example, "vibrate until receiving stop command", "vibrate for 5 minutes", or "vibrate for 20 seconds every minute for the next 15 minutes"). A user interface may, for example, include a smartphone app that, via a BLUETOOTH connection, allows the activation of vibration functionality using, for example, touchscreen or voice input (for example, via a connected smart speaker). A dedicated control interface hereof may, for example, detect hand gestures, hand placement on the outer socket, or include touchless/voice control. Control may also be automated based on measured biological, activity and/or environmental data collected by a smartwatch, smartphone, a sensor system etc. and one or more stored algorithms effecting control based on such measured data.

In a number of such embodiments, the user may turn the device on and off as described above. As discussed above, one or more software algorithms may control the timing and duration of use (for example, via a smartphone app). The user may, for example, be instructed to use the device as needed, turning it on, for example, when they experience phantom limb pain. The vibrations may be set to turn off at a preestablished time. If the user desires continued stimulation, the user may reinitiate a sequence.

Alternatively or additionally, one or more sensors of a sensor system 300 (illustrates schematically in FIG. 2) may provide data/information to circuitry 100 to, for example, provide for more autonomous control and/or improve performance of the devices, system, and methods hereof. Although it is difficult to measure pain or to predict the onset thereof, certain parameters may be measured to ensure suitable or optimized operation of the devices, systems and/or methods hereof and/or be relatable to the onset or severity of pain for a particular patient or a group of patients. A sensor to detect motion or activity such as an accelerometer may be used in controlling activation of one or more vibrators 70 to address resting pain and/or pain related to motion. For example, one or more vibrators may be activated after a certain period of rest/inactivity. That period and/or other control parameters (whether based on sensor measurement or otherwise) may, for example, via adjustable by the user or a clinician via, for example, a BLUETOOTH and/or other communication protocol (in a wireless and/or wired manner). Other sensors such a temperature sensors, heartrate sensors, perfusion sensors, perspiration sensors etc. may be used in determining a physical state of the user/user parameters in activating or controlling the operational parameters (for example, frequency, magnitude, timing etc.) of one or more vibrators 70 hereof. Further, one or more sensors may be provided to measure the operation of the devices, systems, and methods hereof. For example, one or more pressure sensors may be provided to ensure that liner 20 is suitably engaged with or contacting the user's body. Likewise, one or more vibration sensor may be used to ensure suitable operation of one or more vibrators 70 hereof.

One or more sensors of sensor system 30 may, for example, be used in feedback or other control algorithms of the systems, devices and/or methods hereof.

Figure 5A:
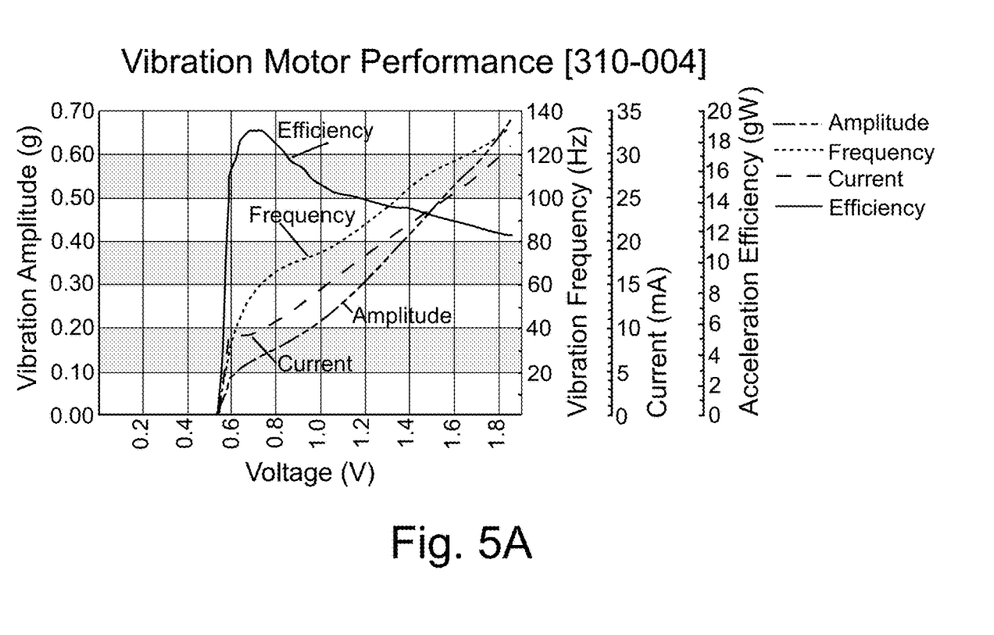
FIG. 5A illustrates performance of 3 mm vibration motors of a device hereof.

The vibration motors (and/or other vibrators) may, for example, be set to a specification determined from research with whole-body and/or other vibration therapy studies. The frequencies used during a number of such studies have, for example, ranged between 20-160 Hz. Negative effects and muscle fatigue may develop in certain cases above this range. In a number of studies, no effects were observed below this range. It has, for example, been found that brief periods of vibrations acting at a frequency between 20-90 Hz resulted in a 2.17% benefit to the musculoskeletal system. With such knowledge, the vibration motors used in number of embodiments hereof are programmed to operate at an effective, yet safe frequency of 90 Hz and amplitude of 0.3 G. Representative PRECISION MICRODRIVES™ motors suitable for use in a number of embodiments of the devices hereof (for example, model #310-004; available from Precision Microdrives of London, UK) have a small diameter of 10 mm, and require 1.2V to operate at a desired frequency of 90 Hz (see FIG. 5A). Such specifications are beneficial to maintaining the device small in size and the patient risk low.

The vibration motors may, for example, be soldered onto LilyPad vibe boards, available, for example, from SparkFun Electronics of Boulder, Colo. (illustrated schematically FIG. 5B) which delivers the programming from an Arduino LilyPad main board via, for example, conductive thread. The LilyPad Arduino may, for example, be programmed to run the vibration motors at a specific frequency and amplitude as well as for a set duration of time. The algorithm may prevent overuse and fatigue of the dosage of vibration at one time. As illustrate in FIG. 5B, vibration device 70' includes an interfacing or connecting pad 72' and a surface-mounted motor 74' operative connected thereto.

Figure 6:
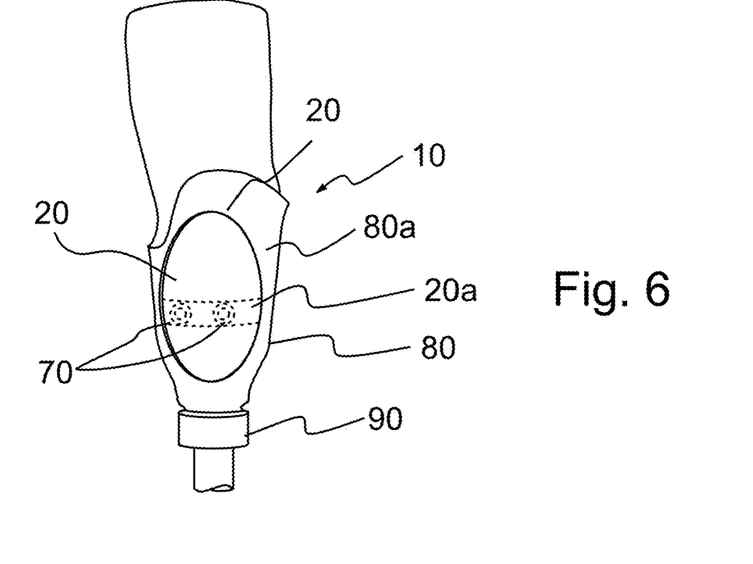
FIG. 6 illustrates a perspective, cutaway view of a user wearing another embodiment of a device hereof in connection with a commercially available prosthetic device/prosthetic socket.

The devices, systems and method hereof provide a non-invasive, non-narcotic intervention that can be applied outside of the doctor's office (for example, during the acute onset of phantom limb pain). The devices, systems and methods hereof need not rely on external hardware (feedback screens, etc.). The vibrations may, for example, be turned off on their own in a number of embodiments. The devices hereof are low profile and easy to use, making them more accessible to a wider population. When incorporated into a prosthetic liner, the system will appear as a typical or normal prosthetic liner. FIG. 6 illustrates a schematic drawing of a prototype device hereof.

Figure 5B:
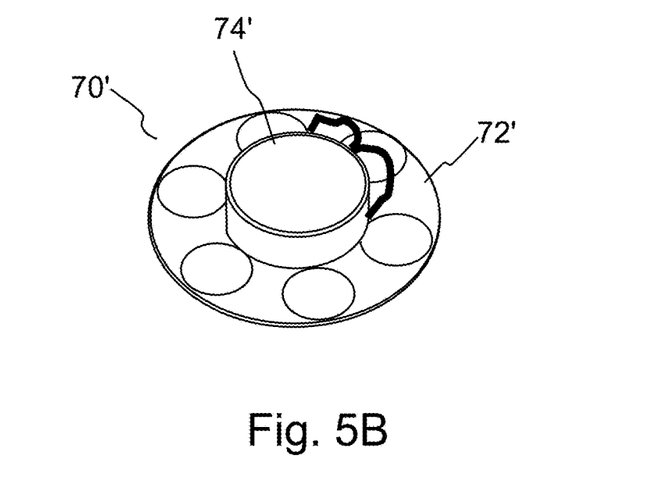
FIG. 5B illustrates a perspective view of a LilyPad vibe board with a vibration motor for use in a device hereof.

The ease of use of devices and systems hereof is demonstrated by the similarity of donning a device or system hereof to donning a typical prosthetic liner, an activity with which an amputee is very familiar. As described above, a liner for a prosthetic device may hold the vibration motor(s) or other vibrator(s) in place as described herein and operate as the vehicle for the vibration therapy. The vibration motors (an example, of which is illustrated in FIG. 5B) provide the vibration. For ease of use, the motors may be incorporated into the liner (for example, by sewing, sandwiching etc.). FIG. 6 illustrates an embodiment of a device or system 10 hereof inside a prosthetic socket 80. The partially cut-away portion 80a of socket 80 provides a view to one embodiment locations at which one or more vibrational motors or other vibrators may be placed. In the embodiment, of FIG. 6 one or more vibrators or vibrational devices 70 may be incorporated in a strip 20a of, for example, silicone material of liner 20.

Figure 7:
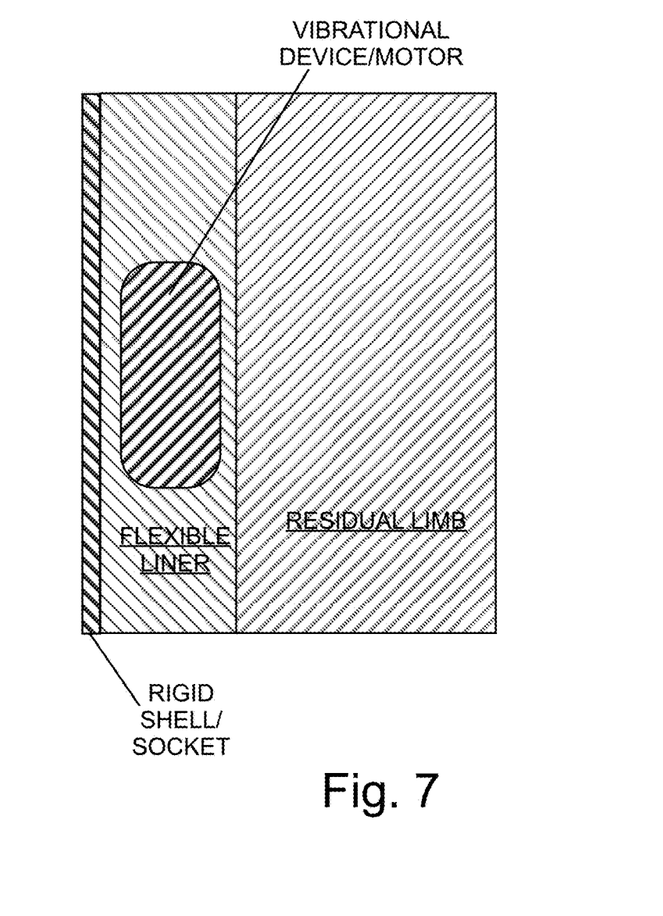
FIG. 7 illustrates schematically an embodiment of the interaction between an amputee's prosthetic socket, an interface or liner hereof incorporating a vibrator and the skin of the amputee's residual limb.

FIG. 7 illustrates schematically an embodiment of patient interface with a device hereof and the prosthetic socket. Because of an intimate fit of the socket with the residual limb in a number of embodiments hereof, it is desirable that vibratory devices hereof exhibit a low profile and conform to the available standards of care to ensure the safety of the users. In the embodiment of FIG. 7, one or more low-profile vibration motors as described herein is/are incorporated within a flexible, polymeric (for example, silicone, polyurethane etc.) interface or liner.

Figures 8A, 8B, 8C, 8D, 8E:
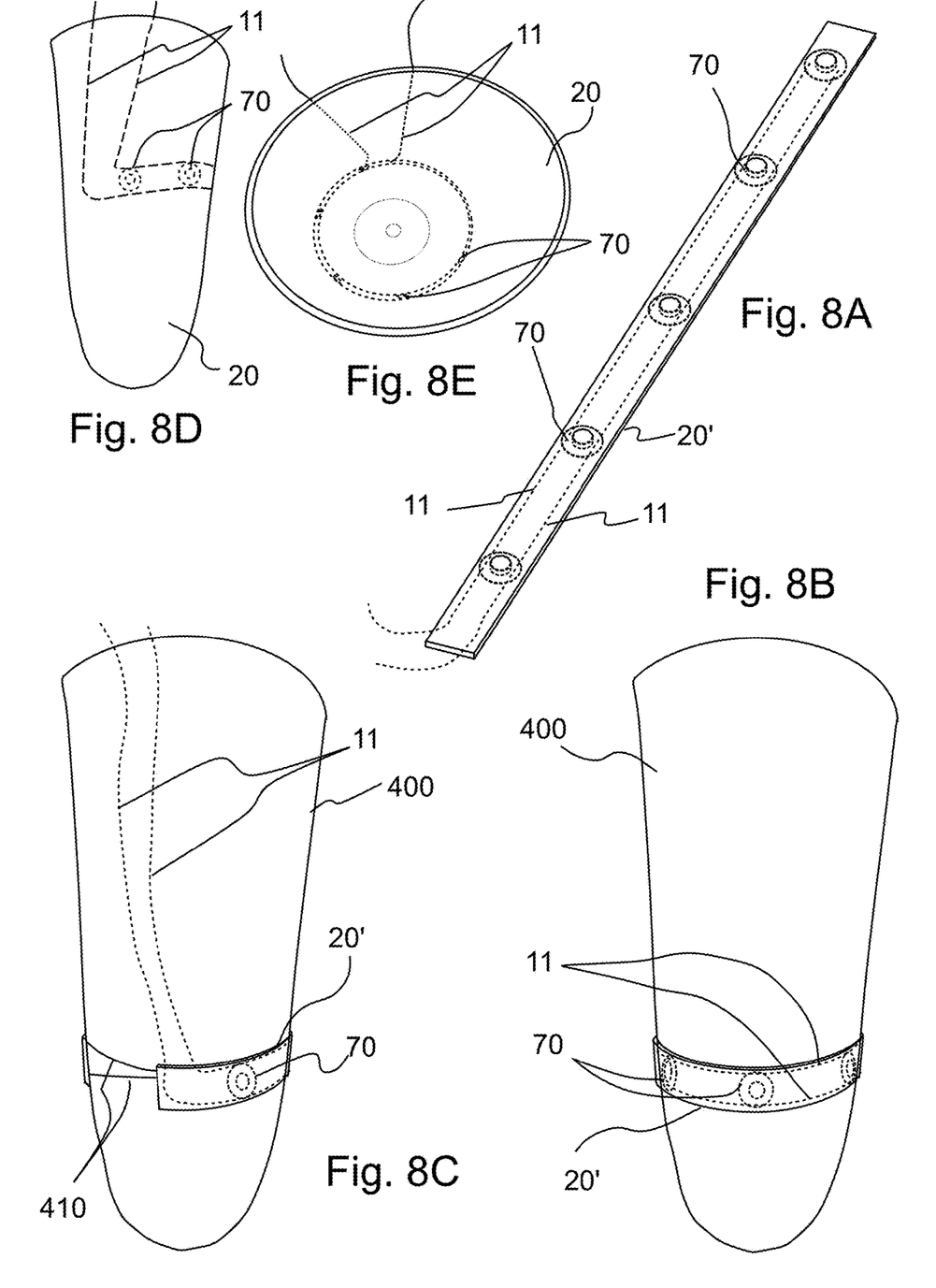
FIG. 8A illustrates a silicone strip including five embedded vibrational motor connected in parallel via conductive thread.
FIG. 8B illustrates a perspective view the silicon strip of FIG. 8A attached to a positive model of a patient's residual limb.
FIG. 8C illustrates another perspective view the silicon strip of FIG. 8A attached to the positive model of a patient's residual limb.
FIG. 8D illustrates a posterior view of a silicone liner or flexible interface for a prosthetic socked incorporating the silicon strip of FIG. 8A.
FIG. 8E illustrates a top view of the silicone liner or flexible interface of FIG. 8D.

FIG. 8A through 8E illustrate fabrication of an embodiment of a prosthetic liner 20 hereof including several embedded vibrational motors 70. Prosthetic liner 20 was shaped using a cylindrical positive model 400 that was formed to have similar dimensions to the patient's residual limb. In a number of embodiments, a silicone strip 20' (see, for example, FIG. 8A) including several vibrational motors 70 and their respective conductive thread 11 were first attached to the positive model 400 as illustrated in FIGS. 8B and 8C.

In forming positive model 400, a large liner was filled with plaster to create a uniform positive model. Once smoothed and an ALIPLAST (a crosslinked polyurethane foam padding available from AliMed, Inc. of Dedham, Mass. USA) layer added, a ⅜" sheet of VIVAK® (a glycol modified polyethylene terephthalate or PETG sheet available from United States Plastic Corp. of Lima, Ohio) was pulled over top. The ALIPLAST was removed from the model once the plastic was cooled to create a ½" gap between plaster mold and the VIVAK when the shell was placed over the model for injection. That methodology created a uniform space for silicone injection. The VIVAK shell was cut and smoothed. Additionally, a 1" diameter hole was drilled in the distal end of the socket, about 2" from the end via which an electric silicone dispensing gun nozzle was placed to force silicone to move upward as injected.

In preparation of strip 20', five LilyPad vibe boards (vibrational motors 70) were tied in parallel using conductive thread 11. Conductive thread 11 replaced the need for wiring inside liner 20, increasing flexibility and ease of donning/doffing. Vibrational motors 70 were then placed in a plastic channel in preparation to create silicone strip 20'. The plastic channel was set so that the strip's width was the same as the gap for the ALIPLAST (½"). Vibrational motors 70 were embedded into silicone strip 20' to keep them from moving when the injection of liner 20 occurs. Strip 20' was peeled from the plastic channel after curing for an hour.

Strip 20' of silicone including vibrational motors 70 was gently glued to positive model 400 using Super 77™ multipurpose adhesive spray (available from 3M of St. Paul, Minn. USA) as illustrated in FIGS. 8B and 8C. Strip 20' was also tied with thin thread 410 (see FIG. 8C) to ensure its placement snugly on positive model 400. Positive model 400, with vibrational motors 70 mounted thereon, was sprayed with Ease Release™ 200 (a silicone releasing agent available from Smooth-On, Inc. of Macungie, Pa. USA) to prevent liner 20 from sticking to positive model 400. The VIVAK shell was placed around positive model 400 and strip 20' including vibrational motors 70. The shell was held in place using eight Chicago Screws around the edges thereof.

An electric silicone dispensing gun (a 400 mL electrically-powered silicone gun) was loaded with a Dragon Skin 10 fast cartridge (a platinum cured silicone available from Smooth-ON). Three cartridges were used to create the final product. When transferring between cartridges, the hole in the VIVAK shell was plugged to prevent the silicone from spilling out while the gun was reloaded.

After letting silicone liner 20' cure for one hour, the VIVAK shell was removed to free liner 20. Resultant liner 20 is illustrated in FIGS. 8D and 8E. In a number of embodiments, liner 20 was an opaque white color, though which motors 70 (illustrated in dashed lines in FIGS. 8A through 8E) could be seen clearly.

In a number of embodiments, liners hereof are formed of a flexible, elastomeric polymer materials such as silicone polymer as described above. Other flexible polymers suitable for use herein include, for example, thermoplastic elastomers, materials including polyurethanes and copolymers such as TECHNOGEL (a polyurethane gel available from Otto Bock of Duderstadt, Germany), DERMOGEL (a silicone liner available from OSSUR of Reykjavik, Iceland), SMARTTEMP (a silicone liner, available from WillowWood of Mt. Sterling, Ohio), and EASYGEL (a polyurethane gel liner available from Alps of St. Petersburg, Fla.).

In a number of embodiment, control system housing unit 150 was separate from liner 20 and was attached to the outside of socket 80 via a hook-and-loop type attachment mechanism or mechanisms 82 (for example, VELCRO available, for example, from Velcro USA Inc. of Manchester, N.H. USA) which are represented schematically in FIG. 4. Control system housing unit 150 houses a processor system 120 (including a microcontroller), a battery/battery charger 110, an indicator light 170 and an ON/OFF switch 160 (see, for example, FIG. 4). In a number of embodiments, an ADAFRUIT TRINKET microcontroller (available from Adafruit of New York, N.Y. USA) was chosen for its size and programmability capabilities. The microcontroller is powered through a lithium ion polymer battery that operates 3.7V and 500 mAh. A 500 mAh battery releases 500 milliamps of current at a specific voltage for one hour before it is discharged. The battery system also powered the Lilypad Vibe motors. The vibrational board motors 70 require 3.3V-5V input. The battery system may be charged using a micro-lipo charger with a microUSB jack. The charger is easy to use for patients, with a red light indicating charging and a green to indicate fully charged. The components were chosen to keep the device small in size and patient risk low.

The systems and liners hereof are very compatible with prosthesis use, as well as easy and quick to activate when a bout of phantom pain occurs. In such instances, there is no need to retrieve a separate device, doff a prosthesis, and subsequent don such a separate device. Such ease of use and quick activation may help reduce both the duration and the intensity of the phantom pain (particularly, in cases where intensity is increasing with time). The systems and prosthetic liners hereof are well suited for the space constraints, applied loads, and cyclic strains experienced during use in connection with prosthetic devices. The system and prosthesis liners hereof provide an intimate fit within a custom prosthesis socket and provide for targeted placement and minimized signal losses (that is, attenuation of the vibration amplitude arising from poor contact between surfaces). In combination, such effects can help reduce the number and size of vibrators, which helps with battery capacity, complexity/failure susceptibility, and costs.

Maintenance care of devices and systems hereof is similar to the care and maintenance of existing prosthetic liners. In general, a light cleaning with antibacterial soap or alcohol may be used. With regard to fitting, circumferences may, for example, be taken 4 cm and 30 cm from the distal end. The McGill Pain Index may, for example, be used to quantify pain relief associated with devices, systems, and methods hereof.

The foregoing description and accompanying drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A prosthetic device, comprising:
   a flexible interface fabricated from a flexible, elastomeric polymeric material and configured to conform to a residual limb of a user,
   a prosthetic socket comprising an outer shell more rigid than the flexible interface and positioned external to at least a portion of the flexible interface, and
   one or more vibrators embedded within the flexible interface to impart vibration to the residual limb, the one or more vibrators comprising one or more vibrational pads wirelessly coupled to an energy source exterior to the flexible interface.

2. The device of claim 1 further comprising electronic circuitry, the electronic circuitry comprising a control system comprising a processor system and a memory system in communicative connection with the processor system.

3. The device of claim 2 wherein the electronic circuitry is configured to communicate with a personal communication device including a control algorithm stored therein to control operation of the one or more vibrators.

4. The device of claim 2 further comprising one or more sensors in operative connection with the electronic circuitry to measure at least one of a parameter of the user, an environmental parameter, or an operational parameter of the one or more vibrators.

5. The device of claim 1 wherein the one or more vibrators have a profile no greater than the thickness of the flexible interface.

6. The device of claim 1 wherein the one or more vibrators have a profile no greater than approximately 6 mm.

7. The device of claim 1 wherein the one or more vibrators comprise one or more vibrational motors.

8. The device of claim 1 wherein the flexible, elastomeric polymeric material comprises a silicone or a polyurethane.

9. The device of claim 8 wherein the flexible, elastomeric polymeric material is a silicone.

10. A method of providing vibrational therapy to a user, comprising:
    placing a flexible interface fabricated from a flexible, elastomeric polymeric material and configured to conform to a residual limb of the user in operative connection with the user's residual limb, the flexible interface having one or more vibrators embedded within the flexible interface to impart vibrational energy to the residual limb;
    providing a prosthetic socket comprising an outer shell more rigid than the flexible interface and positioned external to at least a portion of the flexible interface, and
    imparting vibration to the residual limb via the one or more vibrators, the one or more vibrators comprising one or more vibrational pads wirelessly coupled to an energy source outside of the flexible interface.

11. The method of claim 10 wherein the flexible interface is fabricated from a flexible, elastomeric polymeric material.

12. The method of claim 10 further comprising providing electronic circuitry in operative connection with the one or more vibrators to control operation thereof.

13. The method of claim 12 wherein the electronic circuitry is configured to communicate with a personal communication device including a control algorithm stored therein to control operation of the one or more vibrators.

14. The method of claim 12 further comprising providing one or more sensors in operative connection with the electronic circuitry to measure at least one of a parameter of the user, an environmental parameter, or an operational parameter of the one or more vibrators.

15. The method of claim 10 wherein the one or more vibrators have a profile no greater than the thickness of the flexible interface.

16. The method of claim 10 wherein the one or more vibrators have a profile no greater than approximately 6 mm.

17. The method of claim 10 wherein the one or more vibrators comprise one or more vibrational motors.

18. The method of claim 10 wherein the flexible interface is fabricated from silicone.

19. A flexible interface for use with a prosthetic device, comprising:
one or more vibrators embedded within the flexible interface to impart vibration to a residual limb of a user, the flexible interface being formed from a flexible, elastomeric polymeric material and having a conformation to conform to the residual limb and to an internal wall of a shell of a prosthetic socket of the prosthetic device which is more rigid than the flexible interface and positioned external to at least a portion of the flexible interface, wherein the one or more vibrators are molded within the flexible, elastomeric polymeric material.

20. The flexible interface of claim 19 wherein the flexible interface is fabricated from a flexible, elastomeric polymeric material.

* * * * *